United States Patent [19]

Robson

[11] Patent Number: 4,510,160

[45] Date of Patent: Apr. 9, 1985

[54] INSECTICIDAL PRODUCT AND PREPARATION THEREOF

[75] Inventor: Michael J. Robson, Berkshire, England

[73] Assignee: Imperial Chemical Industries PLC, London, England

[21] Appl. No.: 535,626

[22] Filed: Sep. 26, 1983

[30] Foreign Application Priority Data

Oct. 11, 1982 [GB] United Kingdom ............ 8228983

[51] Int. Cl.³ .................. A01N 53/00; C07C 121/75
[52] U.S. Cl. ............................ 514/521; 260/465 D
[58] Field of Search ................ 260/465 D; 424/304

[56] References Cited

U.S. PATENT DOCUMENTS 4,183,948 1/1980 Huff ............................. 424/304

FOREIGN PATENT DOCUMENTS

A2000764 6/1981 United Kingdom .

OTHER PUBLICATIONS

Pesticide Science, vol. 11, No. 2, 1980, pp. 156–164, Society of Chemical Industry, Bentley et al, "Fluorinated Analogues of Chrysanthemic Acid".

Primary Examiner—Dolph H. Torrence
Attorney, Agent, or Firm—Cushman, Darby & Cushman

[57] ABSTRACT

A novel crystalline material consisting of a enantiomeric pair of cyhalothrin isomers in the form of the racemic mixture and having greater insecticidal activity than cyhalothrin itself is described, together with a process for obtaining the enantiomeric pair of isomers by crystallization from concentrated cyhalothrin solutions in lower alkanols or liquid alkanes.

8 Claims, No Drawings

INSECTICIDAL PRODUCT AND PREPARATION THEREOF

This invention relates to an insecticidal product and methods of preparing it.

The compound α-cyano-3-phenoxybenzyl cis-3-(Z-2-chloro-3,3,3-trifluoroprop-1-en-1-yl)-2,2-dimethylcyclopropane carboxylate, also known by its common name of cyhalothrin, its preparation and insecticidal use is described inter alia in U.S. Pat. No. 4,183,948. This product is a mixture of four isomers which may be conveniently described as follows:

Isomer A—the ester derived from the (+)-cis-acid and the α-(S)-alcohol.
Isomer B—the ester derived from the (−)-cis-acid and the α-(R)-alcohol.
Isomer C—the ester derived from the (+)-cis-acid and the α-(R)-alcohol.
Isomer D—the ester derived from the (−)-cis-acid and the α-(S)-alcohol.

Now isomer A and isomer B have identical physical properties, eg. solubility, melting point, etc. differing only in the direction in which they rotate the plane of polarised light, and as such represent a pair of enantiomers. Similarly, isomer C and isomer D represent a second enantiomeric pair.

It is known from P. D. Bentley et al, Pestic. Sci., 11, (2), 156–64 (1980) that Isomer A is the most active insecticide of the four isomers and that isomers B and D were insecticidally inactive in tests against houseflies (*Musca domestica*). Isomer A is in fact about 25 times more active than the known insecticide permethrin in this test, making it one of the most active synthetic insecticides yet reported. Although it would be desirable to use isomer A alone as the active ingredient of insecticidal preparations, this is not easy to achieve in an economical manner because this requires that the acid and alcohol moieties of the isomer be prepared by chiral synthetic techniques and reacted together in a manner which does not change the chirality. Such techniques have not yet been developed to a level where such a synthesis can be carried out in an economic manner without the co-production of unwanted isomeric products which require to be separated using expensive reagents.

We have now discovered a technique whereby the pair of enantiomers represented by isomer A and isomer B can be readily separated from isomer C and isomer C by physical means not requiring chiral synthesis or chemical resolution, and that insecticidal products of acceptable efficacy can be prepared in an economic manner using the enantiomer pair.

This invention provides in a first aspect a product (hereinafter called the "Product") consisting essentially of the enantiomeric pair of isomers represented by (S)-α-cyano-3-phenoxybenzyl (1R,cis)-3-(Z-2-chloro-3,3,3-trifluoroprop-1-en-1-yl)-2,2-dimethylcyclopropane carboxylate and (R)-α-cyano-3-phenoxybenzyl (1S,cis)-3-(Z-2-chloro-3,3,3-trifluoroprop-1-en-1-yl)-2,2-dimethylcyclopropane carboxylate in racemic proportions and substantially free from any other isomer of α-cyano-3-phenoxybenzyl 3-(2-chloro-3,3,3-trifluoroprop-1-en-1-yl)-2,2-dimethylcyclopropane carboxylate.

By 'substantially free' is meant that not more than 10% by weight of the Product is represented by the combined weight of any other isomers of cyhalothrin.

The Product is a low melting crystalline solid. A typical melting point is in the range 36°–42° C. The actual melting point will depend upon the quantities of isomer C and isomer D present. Cyhalothrin itself (the mixture of all four isomers containing typically from 40–60% by weight of isomers A and B and 60–40% by weight of isomers C and D) is a viscous liquid at the ambient temperature.

When freed from contamination by residual amounts of isomer C and isomer D by recrystallization the Product melts at 41°–42° C. Infra red spectral analysis shows it to consist of a conglomerate of mixed crystals in which each individual crystal is composed of molecules of a single isomer, either isomer A or isomer B, there being approximately equal amounts of crystals of each isomer. It is therefore a racemic mixture.

In a further aspect, the invention provides insecticidal preparations containing the Product and methods of using them to combat and control insect pests. Except for the active ingredient these preparations and methods are identical to those preparations and mixtures set forth in U.S. Pat. No. 4,183,948 referred to above, the disclosure of which is herein incorporated by reference.

In a yet further aspect the invention provides a process for obtaining a crystalline material consisting essentially of the enantiomeric pair of isomers represented by (S)-α-cyano-3-phenoxybenzyl (1R,cis)-3-(Z-2-chloro-3,3,3-trifluoroprop-1-en-1-yl)-2,2-dimethylcyclopropane carboxylate and (R)-α-cyano-3-phenoxybenzyl (1S,cis)-3-(Z-2-chloro-3,3,3-trifluoroprop-1-en-1-yl)-2,2-dimethylcyclopropane carboxylate in racemic proportions and substantially free from any other isomer of α-cyano-3-phenoxybenzyl 3-(2-chloro-3,3,3-trifluoroprop-1-en-1-yl)-2,2-dimethylcyclopropane carboxylate, which comprises the steps of:

(a) forming a solution of cyhalothrin with an organic solvent selected from lower alkanols containing up to 6 carbon atoms and liquid alkanes containing up to 8 carbon atoms, (b) cooling the solution to a temperature within the range −20° C. to +10° C. and optionally adding a quantity of crystals of the enantiomeric pair of isomers to the cooled solution, the added crystals remaining thereafter in the solid undissolved state, (c) maintaining the solution at a temperature within the said range for a sufficient period to allow the crystalline material to precipitate from the solution, (d) separating the precipitated crystalline material from the solution, and optionally, if required, subjecting the crystalline material to recrystallisation until it is substantially free from any other isomer of α-cyano-3-phenoxybenzyl 3-(2-chloro-3,3,3-trifluoroprop-1-en-yl)-2,2-dimethylcyclopropane carboxylate.

Suitable alkanol solvents include lower aliphatic alcohols comprising from 2 to 6 carbon atoms and mixtures thereof. Preferred solvents are ethanol, iso-propanol, butan-1-ol, butan-2-ol, pentan-1-ol, and iso-propanol/t-butanol (1:1), isopropanol/1,2-ethanediol (2:1). Isopropanol is particularly preferred. Preferred liquid alkane solvents are n-hexane and n-heptane.

By a concentrated solution is meant preferably one containing from 2:1 to 1:5, and most preferably 1:1, parts by weight of cyhalothrin: solvent.

The cyhalothrin used as this process may be contaminated with up to 10% by weight of the corresponding trans isomers and (E)-isomers. Preferably cyhalothrin of at least 95% purity is used since this usually provides the Product in higher yield and purity.

If the process is performed using a quantity of added solid Product this usually shortens the time required to effect precipitation of the Product from the solution. (A quantity of Product of sufficient purity to be added may be obtained by subjecting cyhalothrin to high performance liquid chromatography to separate the Product from the other isomers present).

The time required is from several hours to several days, for example 24 hours to 30 days, time to effect a reasonable yield of Product is from 7 to 15 days.

The process is preferably conducted by preparing the solution using slight warming if necessary, and then cooling the solution to a temperature in the range 0° to 10° C. for a first period during which time a substantial amount of Product crystallises, and thus further cooling the solution to a temperature in the range −15° to −5° C. for a second period until crystallisation is substantially complete before collecting the precipitated Product.

If recrystallisation is required to free the Product from other isomers which may have coprecipitated with the Product this may be achieved by using any suitable recrystallisation solvent, for example, the solvents referred to above as useful in the process of the invention.

The invention is illustrated by the following Examples.

In the Examples, isomer A is referred to as the 1R,cis-S isomer, ie. the isomer having the (R) configuration at the carbon atom of the cyclopropane ring attached to the carboxylate group, cis referring to the relationship between the two hydrogen atoms on the cyclopropane ring and having the (S) configuration at the carbon atom bearing the cyano group. Isomer B is referred to the 1S, cis-R isomer, isomer C as the 1R cis-R and isomer D as the 1S, cis-S isomer.

EXAMPLE 1

This Example illustrates the separation of α-cyano-3-phenoxybenzyl cis-3-(Z-2-chloro-3,3,3-trifluoroprop-1-en-1-yl)-2,2-dimethylcyclopropane carboxylate into its constituent pairs of enantiomeric isomers.

The material to be separated was characterised by thin layer chromatographic separation of a sample on a 0.25 mm (analytical grade) silica gel plates using various eluents. There was slight separation of two components corresponding to the two pairs of enantiomers present. The mean $R_f$ values for the two components were as follows:

| Eluent<br>Diethyl ether:n-hexane | $R_f$<br>(average) | $\Delta R_f$ |
| --- | --- | --- |
| 10:90 | 0.22 | 0.025 |
| 15:85 | 0.28 | 0.030 |
| 20:80 | 0.33 | |

Separation of the material was achieved by use of high performance liquid chromatograpy using a Waters Associates System 500 apparatus fitted with a "PrepPAK-500" silica column. This was loaded with 0.5 g of cyhalothrin consisting of a 55:45 mixture of the 1S,cis-S/1R,cis-R: 1R,cis-S/1S,cis-R enantiomer pairs. The eluent was diethyl ether/petroleum ether (boiling range 40°-60° C.) mixture (1:9) and the flow rate was 0.2 liters per minute. Fractions were collected after four recycles. The first fraction was identified by proton magnetic resonance spectroscopy as the 1R,cis-R/1S,cis-S enantiomer pair and the second fraction as the 1R,cis-S/1S,cis-R enantiomer pair. Each fraction had a purity of ca. 98% and together corresponded to about 60% of the amount injected. The p.m.r. data is set out as follows (δ values in CDCl₃):

| 1R,cis-S/1S,cis-R | | 1S,cis-S/1R,cis-R | |
| --- | --- | --- | --- |
| 1.21<br>1.30 | (d) | 1.34 | (s) |
| 1.98<br>2.07<br>2.19<br>2.29<br>2.38 | (m) | 1.98<br>2.07<br>2.19<br>2.29<br>2.38 | (m) |
| 6.38 | (s) | 6.32 | (s) |
| 6.77<br>6.87 | (d) | 6.77<br>6.87 | (d) |
| 6.97–7.50 | (m) | 6.97–7.50 | (m) |

EXAMPLE 2

This Example illustrates the crystallisation of the 1R,cis-S/1S,cis-R enantiomer pair from a solution of cyhalothrin. The crystals used for seeding were obtained by the process of Example 1 above.

455.6 g of a mixture of cis-isomers of α-cyano-3-phenoxybenzyl 3-(Z-2-chloro-3,3,3-trifluoroprop-1-en-1-yl)-2,2-dimethylcyclopropane carboxylate, containing 43.2% by weight of the 1R,cis-S and 1S,cis-R isomers and 56.8% by weight of the 1S,cis-S and 1R,cis-R isomers was dissolved in 460 ml of isopropanol that had been previously dried by distillation from calcium hydride. Dissolution was effected by warming the mixture to approximately 50° C. The solution was cooled to 3° C. whilst stirring with a polytetrafluoroethylene coated magnet, then seeded with a few crystals of a mixture of 1R,cis-S and 1S,cis-R isomers of α-cyano-3-phenoxybenzyl 3-(Z-2-chloro-3,3,3-trifluoroprop-1-en-1-yl)-2,2-dimethylcyclopropane carboxylate. Stirring was continued at that temperature for 9 days then the suspension cooled to −10° C. and stirred vigorously with a polytetrafluoroethylene paddle for 7 days.

The solid which had separated out was filtered off at 3° C., sucked dry, washed once with 100 ml of 40°-60° petroleum ether at 3° C. and dried to constant weight in a vacuum dessicator over phosphorus pentoxide to give 97.6 g of white crystals. This product was shown by capillary gas liquid chromatography to contain 86.9% by weight of a 1:1 mixture of the 1R,cis-S and 1S,cis-R isomers of the starting material. The solid was dissolved in 300 ml of dry 40°-50° petroleum ether, the solution cooled to 3° C. with stirring and a few crystals of a mixture of 1R,cis-S and 1S,cis-R isomers of α-cyano-3-phenoxybenzyl 3-(Z-2-chloro-3,3,3-trifluoroprop-1-en-1-yl)-2,2-dimethylcyclopropane carboxylate, added as seed. After 2 hours the resultant white suspension was filtered at 3° C. and the solid sucked dry. Further drying in a vacuum dessicator over phosphorus pentoxide gave 73.6 g of a white solid containing 92% by weight of a mixture of the 1R,cis-S and 1S,cis-R isomers of α-cyano-3-phenoxybenzyl 3-(Z-2-chloro-3,3,3-trifluoroprop-1-en-1-yl)-2,2-dimethylcyclopropane carboxylate, melting in the range 36°-42° C.

EXAMPLE 3

This Example illustrates the effect of different solvents, ratios of solvent to cyhalothrin, time periods and temperatures on the yield and quality of the Product. The cyhalothrin used contained 42% (±1%) of the 1R,cis-S/1S,cis-R enantiomeric pair of isomers. In each experiment a few milligrams of crystals of the racemic mixture were added after cooling to the desired temperature to assist nucleation. The results are set out in Table I.

TABLE I

| Experiment No | Wt of Cyhalothrin (g) | Solvent/ Volume (ml) | Temperature °C./ Time period (days) | Wt of precipitate (g) | % Content of 1R,cis-S/1S,cis-R isomer pair in precipitate |
|---|---|---|---|---|---|
| 1 | 5.0 | Ethanol/ 5.0 | 3/8 | 0.26 | 84.3 |
| 2 | 10.0 | n-propanol 10.0 | 3/11 | 1.03 | 86.7 |
| 3 | 50.0 | n-propanol 50.0 | 3/12 followed by −10/4 | 8.7 | 91.9 |
| 4 | 5.0 | n-butanol 5.0 | 3/33 | 0.14 | 86.9 |
| 5 | 5.0 | sec-butanol 5.0 | 3/8 | 0.41 | 82.6 |
| 6 | 10.0 | iso-butanol 10.0 | 3/11 | 1.18 | 79.0 |
| 7 | 5.0 | t-butanol/ iso-propanol (1:1) 10.0 | 3/14 | 0.64 | 88.3 |
| 8 | 5.0 | n-pentanol 5.0 | 3/33 | 0.64 | 68.8 |
| 9 | 10.0 | isopropanol 5.0 | 3/11 | 0.97 | 79.1 |

| Experiment No | Wt of Cyhalothrin (g) | Solvent/ Volume (ml) | Temperature °C./ Time period (days) | Wt of precipitate (g) | % Content of 1R,cis-A/1S,cis-R isomer pair in precipitate |
|---|---|---|---|---|---|
| 10 | 10.5 | n-hexane 10.0 | 0/9 | 0.61 | 99.1 |
| 11 | 10.0 | n-heptane 10.0 | 3/22 | 0.48 | 98.6 |
| 12 | 9.6 | n-heptane 10.0 | 3/11 | 0.73 | 96.5 |
| 13 | 10.0 | 2,2,4-trimethylpentane 10.0 | 3/8 | 1.17 | 80.3 |
| 14 | 2000 | n-hexane 2000 | 0/18 followed by −5/7 | 406 | 93.3* |
| 15+ | 200.0 | iso-propanol 200 | 0/7 | 26.5** | 92.0 |
| 16+ | 204.0 | isopropanol 200 | 5/7 | 9.6** | 97.0 |

*After recrystallisation from petroleum ether (40–60° C.); weight 281 g.
**Excludes weight of seed crystals.
+ 4.0 g of seed crystals added.

What is claimed is:

1. The enantiomeric pair of isomers represented by (S)-α-cyano-3-phenoxybenzyl 1R,cis-3-(Z-2-chloro-3,3,3-trifluoroprop-1-en-1-yl)-2,2-dimethylcyclopropane carboxylate and (R)-α-cyano-3-phenoxybenzyl 1S,cis-3-(Z-2-chloro-3,3,3-trifluoroprop-1-en-1-yl)-2,2-dimethylcyclopropane carboxylate in racemic proportions and substantially free from any other isomer of α-cyano-3-phenoxybenzyl 3-(2-chloro-3,3,3-trifluoroprop-1-en-1-yl)-2,2-dimethylcyclopropane carboxylate.

2. The enantiomeric pair of isomers according to claim 1 having a melting point within the range 36° to 42° C.

3. A crystalline material consisting essentially of the enantiomeric pair of isomers according to claim 1 in the form of the racemic mixture of the isomers.

4. An insecticidal and acaricidal composition comprising an insecticidally and acaricidally effective amount of the enantiomeric pair of isomers according to claim 1 in association with an agriculturally and horticulturally acceptable diluent or carrier material.

5. A method of combating insect and acarine pests at a locus which comprises applying to the locus an insecticidally and acaricidally effective amount of a composition according to claim 4.

6. A process for obtaining a crystalline material consisting essentially of the enantiomeric pair of isomers represented by (S)-α-cyano-3-phenoxybenzyl (1R,cis)-3-(Z-2-chloro-3,3,3-trifluoroprop-1-en-1-yl)-2,2-dimethylcyclopropane carboxylate and (R)-α-cyano-3-phenoxybenzyl (1S,cis)-3-(Z-2-chloro-3,3,3-trifluoroprop-1-en-1-yl)-2,2-dimethylcyclopropane carboxylate in racemic proportions and substantially free from any other isomer of α-cyano-3-phenoxybenzyl 3-(2-chloro-3,3,3-trifluoroprop-1-en-1-yl)-2,2-dimethylcyclopropane carboxylate which comprises the steps of:

(a) forming a concentrated solution of cyhalothrin with an organic solvent selected from lower alkanols containing up to 6 carbon atoms and liquid alkanes containing up to 8 carbon atoms, (b) cooling the solution to a temperature within the range −20° C. to +10° C. and optionally adding a quantity of crystals of the enantiomeric pair of isomers to the solution when cooled, the added crystals remaining thereafter in the solid undissolved state, (c) maintaining the solution at a temperature within the said temperature range for a sufficient period to allow the crystalline material to precipitate from the solution, (d) separating the precipitated crystalline material from the solution, and (e) optionally, if required, subjecting the crystalline material to recrystallisation.

7. A process according to claim 6 wherein the solution is formed from cyhalothrin and the solvent in a ratio of from 2:1 to 1:5 parts by weight.

8. A process according to claim 6 wherein the solvent is isopropanol.

* * * * *